United States Patent
Massmann

(10) Patent No.: US 10,071,255 B2
(45) Date of Patent: Sep. 11, 2018

(54) MONITORING SYSTEM

(75) Inventor: Clemens Massmann, Karlsruhe (DE)

(73) Assignee: medic assist GmbH & Co. KG, Bochum (DE)

( * ) Notice: Subject to any disclaimer, the term of this patent is extended or adjusted under 35 U.S.C. 154(b) by 129 days.

(21) Appl. No.: 14/008,125

(22) PCT Filed: Mar. 30, 2012

(86) PCT No.: PCT/DE2012/100087
§ 371 (c)(1),
(2), (4) Date: Dec. 17, 2013

(87) PCT Pub. No.: WO2012/130232
PCT Pub. Date: Oct. 4, 2012

(65) Prior Publication Data
US 2014/0097964 A1    Apr. 10, 2014

(30) Foreign Application Priority Data

Mar. 30, 2011   (DE) .................... 10 2011 001 678

(51) Int. Cl.
*A61N 1/39*   (2006.01)
*A61N 1/372*   (2006.01)
(Continued)

(52) U.S. Cl.
CPC .......... *A61N 1/3925* (2013.01); *A61B 5/0015* (2013.01); *G08C 17/02* (2013.01);
(Continued)

(58) Field of Classification Search
CPC .... G01R 15/18; G01R 15/181; G01R 15/183; G01R 31/3606; G01R 31/361;
(Continued)

(56) References Cited

U.S. PATENT DOCUMENTS 6,169,387 B1 *  1/2001   Kaib ................... A61N 1/3931
                                                         320/132
6,727,814 B2    4/2004   Saltzstein et al.
(Continued)

FOREIGN PATENT DOCUMENTS

EP    1 435 076 B1    4/2005
JP    11-337603 A    12/1999
(Continued)

OTHER PUBLICATIONS

International Search Report of PCT/DE2012/100087, dated Dec. 4, 2012.
(Continued)

*Primary Examiner* — Hai Phan
*Assistant Examiner* — Franklin Balseca
(74) *Attorney, Agent, or Firm* — Smartpat PLC

(57) ABSTRACT

The invention relates to a monitoring system for monitoring a third-party device, in particular a medical device, wherein the third-party device has a signal device for displaying the device status and/or relevant device properties and the monitoring device (2) is associated with the third-party device. Based upon this prior art, in the context of the invention monitoring of the third-party device should be possible and should also operate when the actual status indication of the monitored third-party device is defective. In this connection within the context of the monitoring system according to the invention it is not the status indication of the devices but rather a current proportional to the device status within the monitored third-party device is inductively sensed, evaluated and optionally an emergency signal is detected as a function of the result of the evaluation. The invention also relates to monitoring defibrillators.

9 Claims, 1 Drawing Sheet

(51) Int. Cl.
  *A61B 5/00* (2006.01)
  *G08C 17/02* (2006.01)
  *H04B 5/00* (2006.01)

(52) U.S. Cl.
  CPC ............... *A61B 2560/0271* (2013.01); *A61M 2205/3523* (2013.01); *A61N 1/37276* (2013.01); *H04B 5/0081* (2013.01)

(58) Field of Classification Search
  CPC .............. G01R 31/3689; H04B 5/0025; H04B 5/0056; H04B 5/008; H04B 5/0081; A61B 2560/0266; A61B 2560/0271; A61B 2560/0276; A61B 5/015; A61B 5/0015; A61M 2205/35; A61M 2205/3576; A61M 2205/3592; A61M 2205/3523; A61N 1/37235; A61N 1/37252; A61N 1/3925; A61N 1/37276; G08C 17/02
  USPC .................................................. 607/4, 5, 142
  See application file for complete search history.

(56) References Cited

U.S. PATENT DOCUMENTS

2004/0145488 A1* 7/2004 Schroeder ............... F23N 5/242 340/646
2004/0212344 A1* 10/2004 Tamura ................ A61N 1/3975 320/114
2005/0038482 A1 2/2005 Yonce et al.
2008/0172109 A1 7/2008 Rahman et al.
2010/0179618 A1 7/2010 Marnfeldt et al.

FOREIGN PATENT DOCUMENTS

| | | |
|---|---|---|
| JP | 2006-190118 A | 7/2006 |
| JP | 2009-225835 A | 10/2009 |
| WO | 2011/029101 A1 | 9/2010 |

OTHER PUBLICATIONS

International Preliminary Report on Patentability of PCT/DE2012/100087, dated Oct. 2, 2013.

Yuko Shimada "Trend Forefront of Information Utilization—An object automatically transmitting information Effect on escape from human-wave tactics", from Nikkei Computer, Japan, Nikkei Business Publications, Inc., Mar. 2, 2011, vol. 775, pp. 96-100 with English translation of relevant parts.

* cited by examiner

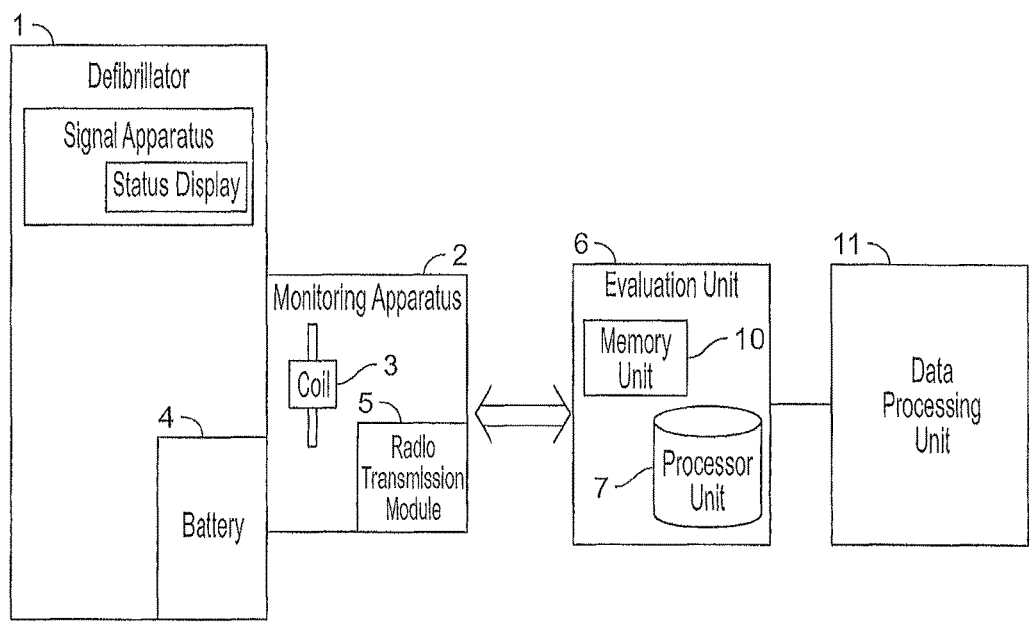

MONITORING SYSTEM

CROSS REFERENCE TO RELATED APPLICATIONS

This application is the National Stage of PCT/DE2012/100087 filed on Mar. 30, 2012, which claims priority under 35 U.S.C. § 119 of German Application No. 10 2011 001 678.3 filed on Mar. 30, 2011, the disclosure of which is incorporated by reference. The international application under PCT article 21(2) was not published in English.

The invention relates to a monitoring system for monitoring a third-party device, particularly a medical device, wherein the third-party device has a signal apparatus for display of the device status and/or relevant device properties, and the monitoring apparatus is assigned to the third-party device, without an intervention in the housing of the third-party device and/or the functionality of the third-party device being connected with this.

Such a monitoring system for acquisition and transfer of status information of a portable medical apparatus is previously known from the European patent EP 1435076 E1.

Although medical apparatuses for monitoring of life-maintaining functions, which are accessed in an emergency, are usually provided with a display that signals the ability of the corresponding device to function, these displays are generally not sufficient in daily use. If, for example, a portable medical apparatus such as a defibrillator is stored in a cabinet, a box, or the like, for example in order to prevent unauthorized access, then an optical or acoustical status display will generally not be observed.

Proceeding from this state of the art, a device is to be developed, according to the previously known solution, with which the displayed status information can be acquired and, if necessary, transmitted to a remote monitoring apparatus. In this connection, it must generally be noted, in the case of such additional devices, that intervention in the already existing device that is to be monitored is not possible without loss of the medical permits in this connection, and should therefore be avoided, if possible. The previously known solution therefore proposes assigning an acquisition apparatus for detecting a status change of the status display of the portable medical apparatus to the medical device, whereby the receiver for detection of the status change is coupled with a transmission device that allows a detected status change of the status display to be sent to a remote receiver.

If understood correctly, the status display monitored according to the European patent is an optical display that is monitored with an optical acquisition apparatus. This presumes, first of all, that an unhindered optical channel is available between the receiver of the monitoring apparatus and the status display. Depending on the position and the storage location of the medical apparatus to be monitored, however, it is difficult, in many cases, to assign an additional device that has unhindered viewing contact with the status display of the monitored device to the monitored medical apparatus. However, even if this is guaranteed, the optical channel can be interrupted for many reasons—for example by scattered light or glare—whereby in this case, an emergency signal would have to be detected even though nothing has changed with regard to the status of the monitored device. Furthermore, in the system known from the European patent, a function disruption of the status display also leads to an emergency signal, even if the function of the medical device is otherwise intact. In the event that the status display of the previously known monitoring device is configured in such a manner that it only actively indicates a disruption in operation, the previously known monitoring device consequently cannot function properly any more in the event of a defective status display.

Proceeding from this state of the art, the invention is based on the task of creating a monitoring apparatus for a third-party device, but particularly for a medical apparatus, the function of which is independent of the function of any status display of the device, and which furthermore functions even if the optical channel between an acquisition apparatus and the monitored device is interruption.

The task according to the invention is accomplished by means of a system having the characteristics of the main claim. Advantageous embodiments of the invention can be derived from the dependent claims 2 to 8.

Because it is not a status display that is being monitored within the scope of the solution according to the invention, but rather, a current that is required in the device to maintain the device-technology functions, monitoring does not depend on the function of any status display of the device. To put it differently: It is not a status display but rather the function of the device itself that is being monitored. This is achieved in that the relevant current is monitored, in contact-free manner, by means of a coil, making use of the induction effect of the current. Since the monitoring apparatus works by means of inductive coupling, the ability of the monitoring system to function is independent of any direct or indirect visual contact with a status display.

A further advantage of the inductive monitoring of the device status consists in that even when the monitoring apparatus is installed, no change or impairment of the user interface of the device being monitored, of any kind, is required. Furthermore, the monitoring provides not only monitoring of the device status but also monitoring of possible changes in the device status, if applicable.

In an advantageous embodiment, the coil for detection of a significant current is disposed in the vicinity of the battery of the third-party device. This arrangement is based on the recognition that the third-party devices to be monitored, particularly medical devices, although they must constantly be ready to function and ready for operation, often are not constantly in operation, but rather are in a readiness position. This readiness state is generally referred to as a so-called sleep mode or power-saving mode, in which only those functions of the device that are required to maintain operational readiness of the device for an emergency are maintained. The ability of the device to function therefore exists if at least the current required to maintain the sleep mode is still being obtained by the device. This current is supplied either by a device-external or a device-internal voltage supply, in other words, in the case of a stand-alone solution and a grid-independent device set-up, by a battery integrated into the third-party device. In order to be able to detect the flowing current here, the coil is disposed in the vicinity of the voltage supply or the battery of the third-party device, or in the vicinity of other conductor tracks significant for purposes of monitoring.

In the case of such an arrangement, it has proven itself if the current flow required to maintain the functions that are active in sleep mode is then also detected with the coil, with the coil disposed accordingly.

In an advantageous further development, the monitoring of the third-party device implemented with the monitoring system does not have to be restricted to a passively reacting monitoring unit, but rather can actively call up a device status display, by means of an actuator integrated into the monitoring unit, which display in turn brings about a current flow that correlates with the display and the device status, or a correlating change in the current flow of the current being monitored with the coil, which change is then detected by means of the coil. In this manner, active and thereby preventive monitoring of the third-party device is implemented.

Because of the inductive effect of the current flow, the coil generates an alternating current or a periodic signal or a pulse signal that is proportional to the detected current. This signal can then be transmitted to an evaluation unit, which might be a remote unit, or can be queried by such an evaluation unit.

In an advantageous further development of the solution according to the invention, the acquisition unit into which the coil is integrated can be provided, for this purpose, with a radio transmission module for wireless transmission and/or remote querying of the signal detected by means of the coil.

In a particularly advantageous use, the monitoring system is used in connection with a defibrillator, which is kept on hand for emergencies, particularly in public facilities. By means of the monitoring system according to the invention, it is ensured that the defibrillator will actually be able to function in an emergency.

In the following, the invention will be explained in greater detail, using an exemplary embodiment that is shown only schematically in the drawing.

This shows:

FIG. 1 a monitoring system for a defibrillator in a block schematic.

The block schematic first of all shows a monitoring system comprising a third-party device to be monitored, here a defibrillator 1, to which a monitoring apparatus 2 having an integrated coil 3 is assigned. The defibrillator 1 is usually kept on hand for emergencies in a publicly accessible building, and is provided, in this connection, with a battery 4 for maintaining its operating state, independent of the general power supply, in order to maintain its ability to function. In this connection, the monitoring apparatus 2 with the integrated coil 3 is disposed in the vicinity of the battery 4, so that the current that flows in the sleep mode of the defibrillator 1, to maintain the basic operational readiness of the defibrillator 1, can be detected by means of the coil 3, by way of inductive coupling.

Because of the induced alternating voltage, the coil 3 generates a periodic signal that is proportional to the monitored current flow within the defibrillator 1. This signal or a signal proportional to the signal, particularly a signal amplified by means of a measurement amplifier, can then be transmitted, in wireless manner, by means of a radio transmission module 5 also integrated into the monitoring apparatus 2, to an evaluation unit 6, which is generally a remote unit. The evaluation unit 6 usually contains a processor unit 7 and a memory element 10 for storing the signals transmitted by the monitoring apparatus 2. In the event that the signals transmitted by the monitoring apparatus 2 to the evaluation unit 6 exceed or drop below predetermined threshold values, an alarm signal is detected by the evaluation unit 6. In this connection, the alarm signal is usually fed directly into a central data processing unit 11, such as a central emergency office or a central service office, in wireless or wired manner. The central service office will then commission a technician, who will either replace or repair the monitored third-party device, whereby this is not an object of the invention to be discussed here.

Above, a monitoring system, particularly for monitoring of medical emergency devices, is described, which system makes it possible to acquire the device status, particularly its operational readiness, independent of the status display of the monitored medical device, and to transmit it to a remote evaluation unit, if necessary, so that medical apparatuses, particularly defibrillators, which are disposed in decentralized, distributed manner, can be monitored from a central unit, with regard to their ability to function, and if necessary, can be repaired, serviced or replaced.

REFERENCE SYMBOL LIST

1 defibrillator
2 monitoring apparatus
3 coil
4 battery
5 radio transmission module
6 evaluation unit
7 processor unit
10 memory element
11 data processing unit

The invention claimed is:

1. A monitoring system for monitoring a non-implantable medical device, wherein the non-implantable medical device has a signal apparatus comprising a status indicator for at least acoustical or visual display of a non-implantable medical device status and/or relevant properties of the non-implantable medical device, the monitoring system comprising:
   a monitoring apparatus assigned to the non-implantable medical device, without an intervention in a housing of the non-implantable medical device and/or a functionality of the non-implantable medical device,
   wherein the monitoring apparatus comprises an inductive receiver, which is assigned to the housing of the non-implantable medical device, and which generates a signal by inductive sensing of a magnetic field created by a sleep mode current which is supplied by a voltage supply and which is present in the non-implantable medical device during a sleep mode in which only those functions of the non-implantable medical device that are required to maintain operational readiness are maintained,
   wherein the signal is significant for at least one of the relevant properties of the non-implantable medical device and/or the status of the non-implantable medical device,
   whereby the function of the monitoring apparatus is independent of the function of the status indicator of the non-implantable medical device, so that not the status indicator of the non-implantable medical device, but rather the function of the non-implantable medical device itself is being monitored.

2. The monitoring system according to claim 1, wherein the inductive receiver is disposed in a vicinity of the voltage supply of the monitored non-implantable medical device, outside of the housing of the monitored non-implantable medical device.

3. The monitoring system according to claim 1, wherein the non-implantable medical device is actively monitored by means of the signal apparatus, in that the monitoring apparatus is coupled with the non-implantable medical device in such a manner that the monitoring apparatus, by means of an actuator, causes the status indicator of the signal apparatus to be triggered, which subsequently can be acquired by means of the inductive receiver of a receiver unit of the monitoring apparatus assigned to the non-implantable medical device, and subsequently is stored in a memory by means of a memory element of this receiver unit and/or is transmitted to an evaluation unit that is disposed at a remote location.

4. The monitoring system according to claim 1, wherein a signal current for voice output of the monitored non-implantable medical device and/or a signal current for a self-test of the monitored non-implantable medical device is monitored by means of the inductive receiver.

5. The monitoring system according to claim 1, wherein the inductive receiver, as a function of the sleep mode current, detects a periodic signal corresponding to the non-implantable medical device status and/or the at least one relevant device property of the monitored non-implantable medical device, which signal is transmitted to an evaluation unit, which is remote, and/or is queried remotely.

6. The monitoring system according to claim 5, wherein the inductive receiver is integrated into an acquisition unit that has a radio transmission module for transmission and/or remote querying of the signal generated by means of the inductive receiver.

7. The monitoring system according to claim 1, wherein the non-implantable medical device is a non-implantable defibrillator.

8. The monitoring system according to claim 1, wherein the magnetic field created by the sleep mode current is inductively sensed through the housing of the non-implantable medical device.

9. The monitoring system according to claim 1, wherein the signal is a periodic signal which is proportional to the sleep mode current.

* * * * *